(12) United States Patent
Baldwin et al.

(10) Patent No.: US 8,168,419 B2
(45) Date of Patent: May 1, 2012

(54) PREVENTION AND REMEDIATION OF PETROLEUM RESERVOIR SOURING AND CORROSION BY TREATMENT WITH VIRULENT BACTERIOPHAGE

(75) Inventors: Douglas Baldwin, College Station, TX (US); Neil S. Summer, College Station, TX (US)

(73) Assignee: Phage Biocontrol Research, LLC, College Station, TX (US)

( * ) Notice: Subject to any disclaimer, the term of this patent is extended or adjusted under 35 U.S.C. 154(b) by 0 days.

(21) Appl. No.: 12/983,136

(22) Filed: Dec. 31, 2010

(65) Prior Publication Data

US 2011/0171719 A1     Jul. 14, 2011

Related U.S. Application Data

(60) Provisional application No. 61/295,142, filed on Jan. 14, 2010.

(51) Int. Cl.
*C02F 3/34*     (2006.01)
(52) U.S. Cl. .................................... 435/235.1
(58) Field of Classification Search ......................... None
See application file for complete search history.

(56) References Cited

U.S. PATENT DOCUMENTS

| | | | |
|---|---|---|---|
| 4,442,895 A | 4/1984 | Lagus et al. | |
| 4,778,653 A | 10/1988 | Kamimura et al. | |
| 5,160,433 A | 11/1992 | Niesen | |
| 6,699,701 B1 | 3/2004 | Sulakvelidze et al. | |
| 6,926,833 B2 | 8/2005 | van Reis | |
| 2009/0180992 A1* | 7/2009 | Summer et al. | 424/93.6 |
| 2010/0243563 A1* | 9/2010 | Summer et al. | 210/606 |
| 2011/0281329 A1* | 11/2011 | Lenherr et al. | 435/239 |

FOREIGN PATENT DOCUMENTS

WO     WO/02/40642     5/2002

OTHER PUBLICATIONS

K. Kamimura, et al: Isolation and Characterization of a Bacteriophage Lytic for *Desulfovrio salexigens*, ***; Applied and Environmental Microbiology, Mar. 1989, p. 645-648, vol. 3.
Brady, et al: Cracking Rock: Progress in Fracture Treatment Design, Oct. 1992.

* cited by examiner

*Primary Examiner* — Shannon A Foley
(74) *Attorney, Agent, or Firm* — Douglas Baldwin

(57) ABSTRACT

Petroleum reservoir souring, caused by microbially induced production of hydrogen sulfide and other sulfur compounds, and the attendant corrosion are remediated by isolating bacteriophage(s) specific for the problematic bacteria (target bacteria) and adding an effective amount of such bacteriophage(s) to water introduced into or resident in the reservoir to kill at least some of the target bacteria. Suitable virulent bacteriophage(s) may be indigenous to the water, located in surrounding areas, or taken from a known banked stock. Means of concentrating solutions of bacteriophage(s) are also disclosed.

13 Claims, 2 Drawing Sheets

PREVENTION AND REMEDIATION OF PETROLEUM RESERVOIR SOURING AND CORROSION BY TREATMENT WITH VIRULENT BACTERIOPHAGE

RELATIONSHIP TO OTHER APPLICATIONS

This application claims benefit of application Ser. No. 61/295,142 filed Jan. 14, 2010.

FIELD OF THE INVENTION

This invention relates to control of souring (hydrogen sulfide production) and corrosion in oil and gas reservoirs caused by bacteria. More specifically, it relates to control of bacteria that produce acid and/or sulfur compounds that cause reservoir souring, fouling and corrosion; control being effected by destruction of targeted bacteria with naturally occurring bacteriophage, virulent for targeted bacteria, particularly sulfate reducing bacteria (SRB) and acid producing bacteria (APB).

BACKGROUND

Microorganisms, including bacteria, are ubiquitous in nature and can have profound negative effects on oil and natural gas recovery. Bacterial fouling of the water needed to hydrofracture ("frac") reservoir rock or to "water-flood," to increase production of oil and gas, can contaminate or "sour" the reservoir by producing hydrogen sulfide ($H_2S$). This decreases the value of the product and can make marginal wells unprofitable. Sulfate reducing bacteria (SRB) produce toxic, flammable $H_2S$, which shortens the lifetime and lowers the reliability of any piping and tankage, and introduces additional safety risks from drill rig to refinery. Acid producing bacteria (APB) produce acids, including sulfuric acid, which lead to additional corrosion.

Bacterial fouling leads to serious problems in the oil and gas industry. Bacterially-evolved hydrogen sulfide sours petroleum reservoirs, elevating risk and devaluing the product, while bacterial production of iron sulfide creates black powder accumulation, causing pipeline blockages. Microbially-influenced corrosion attacks the whole system, from fracture tank to refinery, and degrades fracture fluid additives. In Barnett Shale operations in Texas, water is typically stored in large ponds which are open to the atmosphere prior to the start of fracturing work, allowing the water to become heavily contaminated with bacteria. In addition, bacteria become established in biofilms near the wellbore during shut-in of the well.

The Barnett Shale formation's low permeability requires the use of large-volume hydraulic fracturing technologies to enhance gas production. Other shale formations, such as the Marcellus in the eastern U.S., also require hydraulic fracturing. In a typical "frac" operation, water is collected in portable tanks or large, purpose-dug ponds from a variety of sources, including water wells pumping from aquifers, chlorinated city water supplies, and ponds, rivers, and lakes. Each of these water sources has some level of innate indigenous bacterial contamination that continues growing during the collection reservoirs' exposure to the atmosphere.

Hydrofracturing ("fracing") and "water flooding" is heavily dependent on the availability of water, and a typical horizontal "frac" operation requires one to five million gallons of water. The water is pumped into a production well at very high rates (one to over two hundred gallons per minute (gpm). Droughts such as that affecting the Barnett shale operational area have been common over the past several years. During times of drought, water recovered from previous hydro-fracture operations ("flow-back" or "produced" water) is reused, and mixed with "fresh" water in holding ponds or tanks. This reused water introduces elevated bacterial fouling concentrations and solids loadings. Even in times when no drought exists, the universal use of flow-back water in all "frac" operations is utilized to mitigate the expense and environmental harm done in removing and disposing the highly contaminated waste water and is increasingly being required by regulation.

To counter bacterial fouling and reservoir souring, chemical biocides, commonly hypochlorite bleach, are applied to the fracture water. The cost of the biocide treatment for a single typical "frac" operation can be as much as $50,000. Additionally, the design of recovery systems with sour service alloys, thicker pipe, and heavier valves leads to increases in capital expense.

The scale of the problem is enormous. The Barnett Shale underground natural gas formation extends over 5,000 square miles in north central Texas. A total of 6,519 gas wells with a further 4,051 permitted locations existed as of Aug. 15, 2007. Wells are being drilled within populated areas, such as the Dallas-Fort Worth city limits, where it is vital to minimize risk and environmental impact. The petroleum industry currently spends $2 billion on biocides annually. Broad spectrum biocides require the additional expenditures associated with regulatory compliance. These biocides may remain in the water when it is pumped out of the well, creating waste handling and disposal problems. Understandably, biocide usage in the petroleum industry is facing growing regulatory resistance because of the negative impact on the environment and associated health risks.

As well as requiring enormous expenditures, biocides are not sufficiently effective. Any bacteria that are endemic or are introduced into the formation encounter favorable growth temperatures and conditions during the "frac" and flooding operations, as the large volumes of water pumped downhole result in near wellbore cooling. Wells may be shut in following the operation while surface processing equipment and flowlines are installed, leaving time for bacteria to colonize. Once bacteria become established in a well, they develop biofilms that supply a stream of bacterial contamination downstream the well through water tanks, flow lines and disposal facilities. Biofilms protect the bacteria from the chemical biocides and a program of regular, high volume biocide application must be initiated merely to keep the free-swimming bacteria in check and minimize problem bacterial byproducts. Biofilms themselves are impervious to biocides, and can only be mechanically scoured, as with pipeline "pigs". In addition, there is increasing biocide resistance being observed in hydro-fracture and flood water bacteria.

Other reservoirs are "flooded" with water to enhance recovery—usually oil recovery. In "water flood" operations, injection wells are drilled into the producing horizon and water is pumped—as in fracturing—to displace the oil and/or gas through a formation into other "recovery" well(s) in the same field. Since the water is injected into the reservoir is contaminated with bacteria, similarly to the water used for "fracing," the same problems of souring, fouling, and corrosion occur.

Bacteria also cause a host of additional problems in other sectors of the petroleum industry. Another potential "expense" is the social cost of catastrophic failure. Microbiologically-induced corrosion (MIC) has been a factor in several major oil and gas pipeline incidents, including the wellpublicized 2006 Alaska Pipeline spill. MIC occurs on the insides of pipes or storage vessels, and especially under biofilms.

A better control strategy would be: inexpensively manufactured, environmentally benign, adaptable to changing microorganisms to prevent resistance, targeted towards those microorganisms that constitute the threat, and capable of penetrating and destroying biofilms. Such a control strategy would optionally be able to sense and adjust to the different concentrations of microorganisms encountered, even within the well. The present invention is just such a strategy, providing bacterial control based on bacteriophages, the natural predators of bacteria.

SUMMARY OF THE INVENTION

The present invention is a safe, natural, environmentally sound means of controlling bacterial contamination, corrosion, fouling and souring of oil and gas wells and reservoirs that result from injecting bacteria-contaminated water into a well. More specifically, in one embodiment, the invention is a process for remediation of biofouling and souring of petroleum reservoirs and coalbeds comprising: adding to the water used in flooding and "fracing" operations an effective amount of virulent bacteriophages specific for APB and/or SRB found in the water used in the well. These phages may be produced by concentrating an aqueous solution of virulent bacteriophages from bacteria indigenous to the water. In another embodiment, the invention is a process for replication of bacteriophages comprising: a vessel with an inlet for an aqueous solution containing target bacteria; an inlet for an aqueous solution of bacteriophages virulent for target bacteria; an outlet for a solution containing replicated bacteriophage; wherein the flow rate of the inlet solution containing target bacteria and the flow rate for the solution containing bacteriophages virulent for target bacteria are adjusted to obtain substantially complete destruction of the target bacteria. Other more specific embodiments are disclosed in the Detailed Description of the Invention. The phage-based bacterial control technology of this invention will improve operational efficiencies and prolong the operational life of marginal wells that would ordinarily have been withdrawn from service. It will also decrease the capital costs of creating new wells by maintaining sweet gas production, mitigating the need for sour service pipes and hydrogen sulfide removal apparatus. The ability to universally recycle flowback water will decrease the cost and environmental impact of "frac" and flooding operations. An ancillary benefit will be the improvement of results from "frac" and flooding operations.

DETAILED DESCRIPTION OF THE INVENTION

Figure 1:
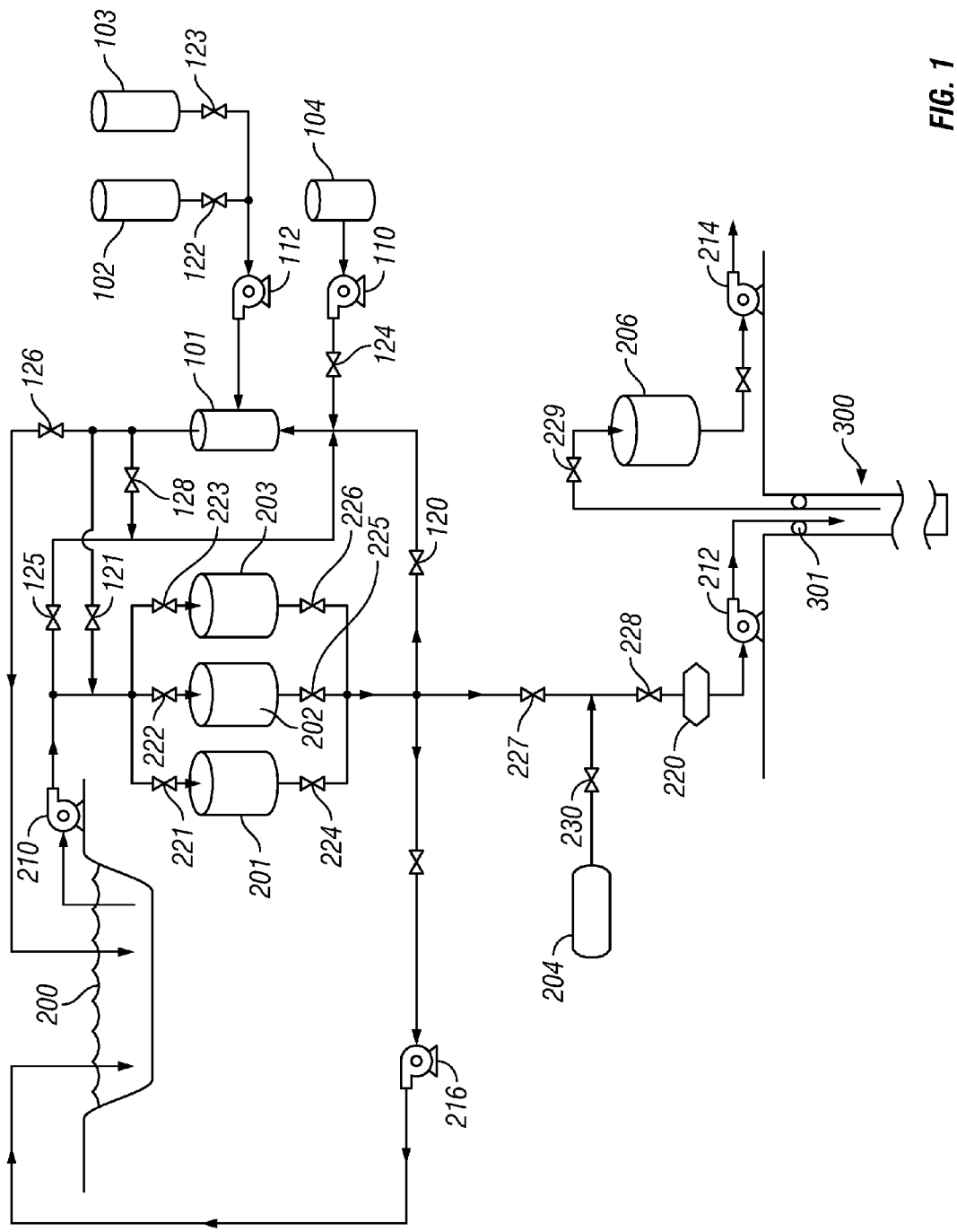
FIG. 1 is a diagrammatic representation of the process of the invention.

Current customary methods of microbial control in oil and gas formations and wells apply broad spectrum biocides, typically by injection into the stream of fracture or flood water at a blender prior to injection into the well. Customary biocides include glutaraldehyde, glutaraldehyde/quaternary ammonium compound blends, isothiazolin, tetrakis(hydromethyl) phosphonium sulfate (THPS), 2,2-dibromo-3-nitrilopropionamide, and bronopol. However, these biocides often have major health risks to humans and all animals in the food chain. THPS and hypochlorite bleach are the most commonly used antimicrobials in the Barnett shale operations area. These EPA registered biocides cannot be introduced into an open pond, as they will permeate into the groundwater, killing aquatic organisms and frequently being consumed by terrestrial animals. All biocides in use by the industry are intentionally employed in a broad spectrum manner. Their effectiveness is determined by conventional culturing methods which merely determine the presence of bacteria and make no attempt to determine genus or species. These methods are labor and material intensive and are essentially unchanged in the past forty years. In typical biocide assessment practices, samples of "frac" water are diluted and cultured in specialized growth medium under various conditions, with and without biocide, for various lengths of time and then compared for bacterial cell density, resulting in more than 40 test cultures each time. There are seasonal variations in bacteria, requiring different growth and test conditions, to which the bacteria may respond differentially. The results take days and, thus, cannot be used for rapid optimization of biocide application. "Water scarcity leads to the reuse of hydrofracture water but when hydrofracture ponds are filled with this already bacterially-contaminated water at the last minute, the assays cannot return results on bacterial activity prior to the water being pumped into the well. The typical field solution to this uncertainty is to apply massively excessive concentrations of sodium hypochlorite. A useful alternative to this would be the instantaneous, on-line determination of bacterial concentrations directing the biocide administration." (*Use of Microbiocides in Barnett Shale Gas Well Fracturing Fluids to Control Bacteria Related Problems*; J. K. Fisher, K. Johnson, K. French and R. Oden, Paper 08658, NACE, International; 2008 Corrosion Conference and Expo.)

The present invention is a process of controlling the problem bacteria by using virulent bacteriophage, instead of synthetic biocides. Bacteriophages are the ubiquitous and natural viruses which infect, are reproduced within, and lyse bacteria. Phage infection is initiated when the tail proteins recognize and adsorb to specific cell surface features of the target bacterial host. This triggers the injection of the phage DNA into the bacterial cytoplasm. The genes in that DNA are expressed by the bacterium's own protein synthesis apparatus, resulting in the synthesis and assembly of approximately 30 to 100 progeny phage particles over the course of minutes to several hours. After, typically, 15 to 60 minutes, the cell explodes ("lysis") as a result of phage-encoded lytic enzymes, liberating hundreds of progeny phage that can then adsorb to new bacterial hosts and repeat the process. In this manner, bacteriophages replicate themselves. Random environmental samples indicate the presence of 10-100 phages for every bacterial cell, indicating $10^{30}$-$10^{31}$ phages in the biosphere.

There are important consequences to this life cycle. First, given a growing bacterial culture to attack, phages can proliferate at unimaginable rates. Within two hours of the addition of a single particle of the classical phage T7 to a laboratory culture of 10 billion *Escherichia coli* cells, more than 99.9% of the bacteria are destroyed and 10 trillion virus particles are generated. There is, thus, a scientific basis for calling bacteriophages "the only medicine that grows" and, in fact, many of the early myths of curative springs or rivers were grounded in the reality that phages existed in these waters at concentrations capable of curing leprosy or cholera (Hankin, 1896). Second, phages are specific for target (or matching) bacteria, because they generally only bind to the type of bacterium that their adsorption device, or "tail", recognizes, and that is encoded in their DNA. Thus, phages are harmless to other bacteria and, obviously, to higher organisms.

Phages do not infect plants or animals and are, therefore, safe to produce, store, handle and apply. Bacteriophages have been declared "Generally Recognized as Safe" for use in human food.

Because bacteriophages reproduce along with the microorganisms that they infect, in the method of this invention, once down-well, they will spread to other bacteria of the same species.

The viscosity additives to "frac" and "flood" water are, ironically, food sources for fouling bacteria. Bacterial degradation of the viscosity additives occurs early in the fracture water tanks and in the subsurface, causing premature viscosity drops and fracture closing. When a panel of phage cocktails is mixed into the fracture fluids, these premature failures may be abated or avoided, forestalling otherwise rapid decline of the wells and retaining production rates. Phage products may also impart a level of immunity to the reservoir, thereby extending the commercial life of a producing well.

In one embodiment of this invention, as more fully detailed below, high concentration virulent phage solution is first injected into a well, followed by the bulk of the "fracing" water, thus enhancing the immunity of the reservoir by filling the fractures with the highest level of virulent phage biocide. Where the "fracing" is conducted in stages or segments— where a segment of the well is fractured (after perforating if there is casing) and then temporarily sealed—higher concentrations of phages will be injected into each segment as the segment is fractured. High concentration of phages is highly desirable to initiate infection of problematic bacteria.

Other petroleum resources will be similarly positively impacted. Petroleum reservoirs will be prevented from souring during water flood operations, as phage products will kill SRB and impart a persistent level of immunity to the reservoir. Phages can also be used to treat existing reservoirs. Thus, the use of phages in accordance with this invention will reduce completion costs, workovers and re-completions, and, most importantly, overall production costs due to capital and operational expenses associated with bacterial fouling, corrosion control and repairs.

As used herein, the following definitions apply: A phage cocktail includes multiple, receptor independent phages for each target bacterial host. This is different from a phage panel, which is a collection of phages chosen to cover as wide a host range as possible. For the purposes of this invention, the phage treatment of waters will consist of a panel of phage cocktails, that is, there will generally be at least two phage cocktails for each of several target SRB bacteria, and two virulent phages for each target bacteria. Since some SRB phages are known to be polyvalent—effective against more than one strain of SRB—there may not need be a separate cocktail for every strain of target bacteria. This panel of cocktails is designated herein as phage "multi-panel".

A somewhat typical flow scheme for a "fracing" operation (as, for example, in a Barnett Shale gas well) may be understood by reference to FIG. 1. Water from a lined storage pit 200 is pumped into one of several 500 bbl temporary storage tanks, 201, 202 and 203, or the tanks are filled directly from other water sources. Water in the storage pit may be tanked in, produced from water well(s), river water, natural run off water, or any other convenient source. For reference, a half acre pit of 6 ft average depth contains 488,779 gallons. Most of the water sources will be heavily contaminated with bacteria. Since the pit is open it will have additional air-borne and run-off bacterial contamination with numerous and varied bacterial strains.

Water from the temporary storage tanks is mixed with chemical additives and proppants, to hold the fractures open (usually sand or ceramic beads), and with biocides from tank 204 (usually a tank truck). Water and additives are mixed in mixer 220 and picked up by high pressure pump(s) 212 for high pressure injection into a wellbore 300. This high pressure water causes fractures or cracks in the gas bearing rock or shale formation allowing the gas to be released to exit the well through the well bore. The proppants help hold the fractures open.

The well bore 300 is sealed up-well of the to-be-fractured area by packer(s), 301, to maintain pressure in the wellbore during "fracing". Water pumping rates range from about 10 bbl/minute to as much as 200 barrels/minute (420-8,400 gal. per min.). Rates of 70-80 barrels/minute are typical in Barnett Shale wells. The "frac" water may be injected in one or more stages, or may be injected into individual segments of the well bore. For example, the segment of deepest portion of the well may be sealed and fractured, then filled with sand and the tools pulled back to seal and fracture a second segment, and so on. For the purposes of this invention, each of these segments may be considered a separate "frac" operation.

After the desired amount of water has been pumped into the well for fracturing, the well sits idle while production equipment is installed at the well head. Thus, the well may sit with "frac" water in it for days or months. During this time bacteria grow and produce acid and sulfur compounds in the reservoir formation. Moreover, these bacterially produced compounds will cause further problems when the water is returned to the surface, including microbially induced corrosion (MIC) of top side equipment. When the surface production equipment is installed, the injected water is allowed to return (flowback and "produced" water) to the surface for disposal, shown in FIG. 1 as stored in tank 206. In "fracing" operations, generally about 20-40% of the injected water remains in the formation. The flowback or "produced" water contains oil, salts, contaminates, and increased bacterial concentrations, and is generally problematic for recycle. In a study of biocides in several Barnett Shale wells, the bacteria level increased at least one order of magnitude from the source water, e.g. from $1 \times 10^6$ bacteria/ml to $1 \times 10^7$ pfu/ml. Increasingly, recycle, and treatment of the "produced" water, is required.

According to this invention, bacterial control is accomplished by adding an effective amount of virulent bacteriophage solution, as in a phage multi-panel, to the "frac" water as, for example, by adding it to the water storage pit (pond) or temporary storage tanks. In water flood operations, to enhance production, or in an already soured reservoir, the bacteriophages will be added to the water or injected with the water to combat SRB, and will prevent further degradation and production of $H_2S$. If phage multi-panel is added to the "frac" water pond, it is preferred that it be added under the surface of the water (SRB are anaerobic), and added slowly in discrete locations—such as can be accomplished with a soaking hose or similar injection means. If the phage multi-panel is distributed in discrete volumes, rather than by rapid mixing, the phage concentration level remains high in the area immediately surrounding the injection for sufficient time to allow phages to infect target bacteria. The rate at which phages attach to, infect, and lyse target bacteria is highly dependent upon the concentration of phages and target bacteria. Generally, it is desired that each be at least about $1 \times 10^5$ pfu/ml. By slowly seeping the phage multi-panel into the water, the phages form a pocket of high concentration surrounded by concentrated bacteria. As the phages infect and lyse target bacteria, the number of phages multiply exponentially; thus, the phages diffuse through the water in a kind of wave of concentrated phage attack of the surrounding bacteria. If, on the other hand, the phage multi-panel is rapidly and thoroughly mixed with the "frac" water in large volumes, the concentration is greatly reduced and the phage infection of bacteria is slowed to unacceptable levels. Thus, a means of slowly adding the phage solution, such as a type of "soaking hose", is desirable.

Because the quantity of water is so great, large amounts of bacteriophage solution will be needed if the entire "frac" water is to be treated. Moreover, phages are not mobile—they have no mechanism for moving about to find and attack target bacteria. Phages must be brought into physical contact with target bacteria. Therefore, in one embodiment, the needed virulent phages are generated on-site. This is accomplished in a phage proliferator/concentrator process.

Phage Proliferation and Concentration

In order to produce a sufficient amount of bacteriophages to treat the large volume of water, phages may be replicated and concentrated on site. Fortunately, propagation of virulent phages is achieved by the bacteriophage injecting itself into its matching bacteria and replicating itself at the same time as it destroys the bacteria—as is also explained in more detail below. Bacteriophage proliferation for use in treating the "frac" or "flood" water is illustrated in FIG. 1. In general it is preferred, and sometimes necessary for the entire proliferation/concentration system to be blanketed with a non oxygen gas. Nitrogen is preferred, since the SRB are aerobic and will be killed if there is significant oxygen in the system.

Vessel 101 is a proliferator/concentrator. Water containing target bacteria is pumped into vessel 101 through valve 120, where it is mixed with bacteriophage panel or multi-panel virulent for the target bacterial strains, shown as being pumped out of vessel 104 with pump 110 through valve 124 to be mixed with the incoming bacteria-containing water. Some forms of SRB will be substantially destroyed by their specific virulent phages in less than 20 minutes. The concentrator vessel is sized to provide a flow rate of concentrated bacteriophage solution sufficient to treat the desired volume of "frac" water. A 4 ft diameter vessel will have a volume of 12.6 $ft^3$/ft of height. A 6 ft diameter vessel will have 28.3 $ft^3$/ft. Thus, a 4 ft diameter vessel, 8 ft tall, will contain 100.8 $ft^3$, and a 6 ft diameter vessel, 8 ft tall, will contain 226.4 $ft^3$.

A flow rate of 9.3 gpm in the 4 ft. diameter reactor, and 37.7 gpm in the 6 ft. diameter reactor, will provide 20 minute residence time (equivalent to the time needed for a substantially complete kill of some strains of SRB bacteria). Residence time will, of course, vary with flow rate, and can be suitably adjusted to provide sufficient time for phage replication for each phage species.

Concentration of bacteriophage in solution leaving vessel 101 depends upon the concentration of target bacteria in the incoming water. When matching bacteria are present, some phages may be replicated by a factor of about 20:1. Therefore, for example, when the incoming water contains $2 \times 10^6$ pfu/ml, the outgoing stream will contain $4 \times 10^7$ pfu/ml. If the replication is 100:1, then the outlet stream will have a phage concentration of $1 \times 10^8$ pfu/ml—a two orders of magnitude increase. The phages will continue replicating themselves so long as a sufficient concentration of target bacteria remains in the water. Thus, the replication will continue when the outgoing concentrated phage solution is mixed with bacteria-containing "frac" water.

Initially, the proliferator/concentrator is fed with a solution of bacteriophage multi-panel (mixture of virulent phages) that has been separately generated—shown in vessel 104 and passed to the proliferator/concentrator through valve 124 by pump 110. Once the concentrator is functioning, phages may be supplied by recycle of a portion of the output stream through valve 128. The amount of recycle will preferably be sufficient to provide a phage-to-target-bacteria ratio between 1 to 0.001. In general, the recycle will contain about 20 times the concentration of phages as the concentration of target bacteria in the source water since some SRB phages will replicate themselves in target bacteria about 20:1. Some of the concentrated phage solution may be stored for future use, as in one of the temporary storage tanks, 201, 202, and 203.

In FIG. 1, vessels 102 and 103 are used for culturing target bacteria which may optionally be added to the proliferator/concentrator 101 to increase the concentration of incoming bacteria and, hence, the amount of phages produced. Such supplemental bacteria may also be varied to generate a desired concentration of phages in the output stream. Culturing of bacteria may be conducted on-site or at an off-site, centralized location and brought to the treatment site. Alternatively, target bacteria may be concentrated from the "frac" water or other source in a tangential flow filter system. Such a system is illustrated in FIG. 2.

Figure 2:
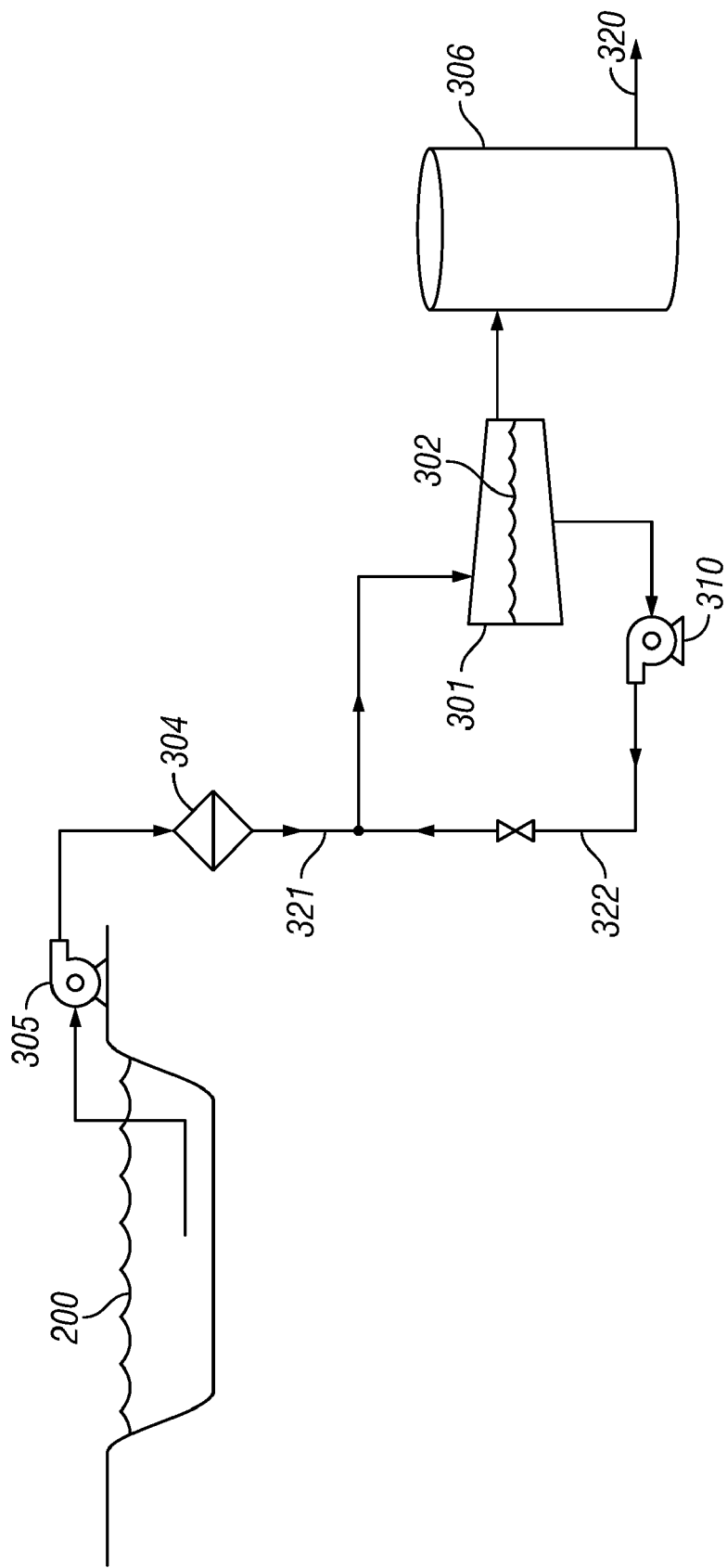
FIG. 2 is a diagrammatic representation of one aspect of the process of the invention.

Referring to FIG. 2, water is pumped from the "frac" water pond 200 (or other suitable storage, as would be required in some water flood operations) by pump 305 to filter 304—a coarse filter to remove larger particles and trash. From filter 304 the water passes by conduit 321 to tangential flow filter 301, having a filter screen, 302, of about 0.2 micron. The screen is sized to hold back SRB and let smaller particles pass. The filter water may be recycled to the filter by pump 310 (through conduit 322). The filtrate passes to tank 306, where it may be directed as needed by conduit 320.

The illustration in FIG. 2 shows the water source as the "frac" water pond. It may, of course, be any suitable source. In one embodiment, the source will be the "produced" water from the well (see vessel 206 in FIG. 1). In general, the "produced" water will contain salt (NaCl) and some target bacteria, which may be halophilic. If it is found that the offending target bacteria are halophilic, and target SRB from the "frac" water does not survive in the salt water environment of the formation, it will be desirable to isolate target halophilic bacteria recovered from the reservoir. Such bacteria can also be cultured, as described above, by using a brine culture solution.

In FIG. 1, vessel 101 contains phages virulent against the target or host bacteria used to start the process. It may be replenished from the concentrated outflow of the phage concentrator 101 or from an external source.

Thus, in operation, the phage concentrator will take in "frac" water from one of the storage tanks 201, 202 or 203 through valve 120 or, alternatively, directly from storage pit 200 through valve 125.

Concentrated phage solution may pumped to one of the temporary working tanks 201-203 through valve 121, or returned to the water storage pit 200 through valve 126. In either case, the phages will continue replicating if there are sufficient target bacteria present, substantially destroying most of the target bacteria.

In one embodiment, more concentrated phage solution will be first pumped into the well before the bulk of the "frac" water is injected. For example, if the bulk of the treated "frac" water contains $1 \times 10^6$ virulent pfu/ml, the first solution will be about $1 \times 10^7$ to $1 \times 10^{10}$ pfu/ml. This allows the fracture formation to be saturated with a "packet" of high concentration virulent phage solution to mitigate bacterial growth in the well. In general, this first solution will be about 0.01 to 10%, preferably about 0.1 to 5%, of the total "frac" water injected.

All the vessels 101, 102, 103, and 104 are constructed of simple materials. They only need to be sufficiently strong to hold the solutions. Corrosion is not a particular problem, although they should be able to contain oily "flowback" water, which will include salt and chemical additives. It is desirable that they be able to be washed and sterilized with bleach solution. It is also desirable that they be able to be "blanketed" with a non-oxygen gas. Generally, most plastic materials used for tanks and vessels are suitable, including fiberglass, polypropylene, polyvinyl chloride, and polyurethane. Stainless steel will also be suitable. Other commercially available materials will be obvious to those skilled in the art.

Since bacterial growth, and to some extent phage proliferation, is temperature sensitive, there is provided in one embodiment means for heating either the inlet streams to the vessels or heating the contents of the vessels. The streams may be heated by heat exchange, electrical heaters, or any other suitable means known in the art. The contents of the vessels may be heated with electrical or steam heaters or other suitable heating means known in the art.

These vessels are not especially heavy, and the equipment is not extensive; therefore, in one embodiment the proliferation/concentrator equipment—vessels 101, 102, 103, and 104, and associated pumps, valves and piping—are mounted on a movable platform so that they can easily be transported from well site to well site. These can be mounted on skids (that can be lifted onto a truck bed), or on a trailer or truck bed.

In another embodiment, this invention is a composition comprising a concentrated amount of bacteriophage virulent for prokaryotes, i.e. APB and/or SRB found in water sources used in oil, gas, and coalbed well flooding and "fracing". The composition will contain between $1 \times 10^4$ to $1 \times 10^{12}$ pfu/ml. In one embodiment, the target bacteria are SRB.

Identifying target bacteria and virulent phages and culturing bacteria and large scale bacteriophage are necessary steps in this invention and explained more fully below.

1. Identifying Target Bacteria:

Target bacteria are identified by sampling the source water and/or biofilm. From samples, the target bacteria can be isolated and characterized, to some extent based on what is generally already known about the causes of corrosion, souring and fouling. From these samples, virulent bacteriophages are identified for target bacteria and bio-corrosive organisms, i.e. SRB and APB. Sufficient phages are then isolated to effectively lyse the target bacteria, and an effective amount of phage solution is added to the water used for "fracing" a well formation. SRB comprise *Desulfovibrionaceae* selected from the group consisting of *D. vulgaris, D. desulfuricans* and *D. postgatei*. In yet another aspect, the bio-corrosive organisms comprise *Caulobacteriaceae* selected from the group consisting of *C. Gallionella* and *Siderophacus*. A wide variety of organisms may be targeted, e.g., archaebacteria, eubacteria, fungi, slime molds, and small, bio-corrosive organisms. The SRB group of bacteria reduces sulfates to sulfides, releasing sulfuric acid and hydrogen sulfide as byproducts which react with iron to form the characteristic black precipitate iron sulfide. Hydrogen sulfide gas is not only extremely toxic and flammable, but it causes souring of the petroleum product, resulting in reduced quality and increased handling cost. The term "SRB" is a phenotypic classification, and several distinct lineages of bacteria are included under this umbrella term. Target bacteria include members of the SRB including, without limitation, members of the delta subgroup of the Proteobacteria, including *Desulfobacterales, Desulfovibri-onales*, and *Syntrophobacterales*. Also targeted are the APB bacteria that produce acidic metabolites. This specifically includes sulfur-oxidizing bacteria capable of generating sulfuric acid. This includes, without limitation, sulfur bacteria such as *Thiobacilli*, including *T. thiooxidans* and *T. denitrificans*. Targeted bacteria further may include bacteria populations and isolates, and further includes corrosion-associated iron-oxidizing bacteria. Also included are isolates of the *Caulobacteriaceae* including members of the genus *Gallionella* and *Siderophacus*.

Still further, bacterial populations may work synergistically with the bio-corrosive bacteria described above. These include members of microbial consortia exhibiting biofilm formation activity. Such biofilms can provide the anaerobic microenvironment required for the growth of corrosion promoting bacteria. As such, the target of phage treatment can include not just the corrosive metabolite producing bacteria, but also any bacteria involved in forming the microenvironment required for corrosion. Additionally, biofilm producing bacteria involved in the biofouling process are included in the category of targets for phage remediation. Biofilm forming genera of bacteria include *Pseudomonas* or *Vibrio* species isolated in affected containment systems.

Bacterial populations responsible for biofilm blockage may also be selected for phage treatment. All bacteria that are to be targeted for phage treatment are part of the selected bacterial subpopulation.

2. Culturing Target Bacterial Strains:

The target bacteria are cultured by means well known in microbiology. Any means of culturing bacteria that promotes growth of the bacterial population are suitable. For example, liquid cultures of *D. vulgaris* can be grown in ATCC medium1249 Modified Baar's medium for sulfate reducers. Plate cultures of *D. vulgaris* are then grown on ATCC medium: 42 Desulfovibrio medium. Cultures have been grown at either 22° C. or 30° C. in anaerobic GasPak jars (VWR). *D. vulgaris* growth forms a characteristic black precipitate in media containing ferrous ammonium sulfate, an indicator of sulfate reduction.

Sufficient bacteria can be grown and enriched in a relatively small container. Therefore, it is preferred that the initial culturing of bacteria be conducted on site or in-situ, as for example, as illustrated in FIGS. 1 and 2. Larger quantities, as are needed for large scale production of phages, are preferably grown in a centralized location having the equipment and resources needed.

If the target SRB bacteria are halophilic, it will be necessary to adjust the culture by addition of NaCl.

3. Identifying Virulent Phages for Target Bacteria:

The geographic distribution of industrial bacterial contaminations is world-wide and transverses many geographic and geological boundaries. Similarly, the sources of phages for controlling bacterial infestations include any site where bacteria are found and, thus, transverses many geographic and geological boundaries. While existing phage stocks will be screened for activity on target bacteria, new phages will also be isolated from the same site or location where the bacteria pose a problem, such as soils, stagnant waters, indigenous water and the like. As the natural predators of bacteria, populations of bacterial phages will be most abundant near abundant sources of their prey. Therefore, the process of identifying phages specific for any bacterial population is to first identify an environmental site where that bacterial type is abundant. This means that there is not one environment that will serve as a source of phages for all target microbes. Instead, the exact environmental sample will vary from host strain to host strain. However, there are general guidelines for identifying the environmental sample most likely to yield desired phages. An ideal sample is marine or freshwater sediment from an environment favorable for the growth of the host bacteria. Specific physiochemical properties of the sediments are important. While the exact parameters will vary from host to host, variables to consider include salinity, temperature, pH, nitrogen or eutrophication, oxygen, and specific organic compounds. An example, which is not intended to be a guideline for all protocols, would be the identification of phages active against a sulfate reducing bacterium (SRB) such as Desulfovibrio. Sediments enriched in SRB are characterized by a black anoxic layer and the production of odiferous volatiles such as hydrogen sulfide. These sediments are common in areas experiencing eutrophication in concert with the resulting oxygen depletion. Therefore, a sample likely to possess SRB specific phages will be a black, hydrogen sulfide producing sediment collected from waters rich in organic compounds.

The choice of a sample site for phage isolation is customized to a specific host bacterium. Phage isolation sites may include any body of water (natural or man-made), sediments, or soil samples. Phage isolation sites may also include man-made structures such as the target water source, containment or settling tanks, creeks, and ditches. Within the man-made structures, the sludge-like deposits composed of organic and inorganic sediments that have settled at the bottom of the structures are often the optimal sampling site for isolation. Phages for any given host can be found at the same conditions relative to salinities, temperatures, pH, pressure, nitrogen concentrations, and oxygen levels that are favorable to the growth of the host bacteria. Bacteria vary greatly with regard to carbon source utilization, similarly phages that infect these bacteria can be found in these environments regardless of carbon source being utilized by the bacteria. Similarly, bacteria and phages vary greatly with regard to tolerance and utilization of industrial waste materials such as metals, heavy metals, radioactivity, and toxic chemical wastes including pesticides, antibiotics, and chlorinated hydrocarbons.

As an alternative to identifying samples based on physiochemical properties, molecular tools are used to identify sediments possessing wild populations of bacteria similar to the target bacteria. These methods typically require some level of purification of DNA from the environmental sample, followed by the detection of marker DNA sequences.

The most straightforward of these are polymerase chain reaction (PCR) based technologies that target 16s rDNA sequences. These can be analyzed by methods such as denaturing gradient gel electrophoreses (DGGE) or by DNA sequencing.

4. Isolation of Novel Phages Active Against Target Bacteria:

It is necessary to match collected phages to a target strain of bacteria; matching in the sense of obtaining a phage sample that is specifically virulent (lethal) for the target bacteria strain. Matching is accomplished by identifying the bacteria strain and empirically applying a phage sample until a clearing of the bacteria is obtained. Not all bacteria will be destroyed because a minimum level is required to initiate infection and clearing. It may also be accomplished without ever identifying the bacteria strain by empirically finding a matching virulent phage from collected or stored phage samples. These empirical methods are more research intensive than specifically identifying the bacteria and/or the virulent phages, but are equally effective for the purpose of this invention.

Using criteria discussed above with respect to the individual characteristics of the target bacteria, an appropriate environmental site will be identified from which phages can be isolated. The primary methodology used to isolate these phages is an enrichment method. Sediment, sludge, or soil samples from the environmental site will be mixed with a solution containing salts and peptides. The exact composition of this solution can vary but, in general, will approach the same composition as Lysogeny Broth (commonly referred to as LB media: per Liter—10 g tryptone, 5 g yeast extract, 10 g NaCl).

The ratio of sample to LB will vary, with the goal of producing a thick, turbid sludge. This is shaken for several hours, and a sterile rinsate is produced from it by sequential centrifugations and filtrations to remove solid material greater than 0.2 microns. This is termed a "rinsate" and the rinsate is then supplemented with concentrated fresh bacterial media (which will vary depending on the exact bacterial host being grown). A small amount of the host is then added to the rinsate/media mix and allowed to incubate for one to several days depending on the growth rate of the host. Incubation conditions including shaking, media temperature, and oxygen levels will be those that promote growth of that particular host. After incubation, chloroform will be added to 0.01% and the solution will be sterilized by sequential centrifugation and filtration to remove intact bacterial cells. This solution is termed an "enrichment". Phages in the "enrichment" are assayed for by several different methods including the plaque assay, liquid culture lysis, or visualization by electron microscopy. The final product is an aqueous solution containing phage particles in a weak phosphate buffer with minimal bacterial cellular debris.

5. In-Situ Test of Identified Killer Phage Strains:

Matching of the identified phages and target bacteria or biofilm in isolation is critical to the success of the process of this invention and must be validated in "real life" conditions of the environment in which it is to be used. Thus, the matched phages are tested in the water conditions that exist. This is suitably done in a side-stream or aliquot of the water system to be treated. A suitable means for this test, for example in the "frac" water pit, is to pump a stream of the water source into a suitably sized container or side loop for sufficient time to allow it to come to equilibrium with the water source. The identified phages are introduced into the stream (either batch wise or in continuous flow) and tests are made to determine if the population of target bacteria is reduced.

6. Preparing Suitable Quantity of Identified Phage Multi-Panel to Treat the Target Water System:

The treatment phage multi-panel consists of a mixture of virulent phages that have been found to "match" target bacteria and biofilm to be treated. Sufficient phage solution must be manufactured to provide an effective amount and concentration to significantly reduce the target bacteria population, or at least to initiate phage proliferation in a system, as described in reference to FIG. 1.

For this, phages exhibiting bacteriolytic activity against target bacteria will be selected. Phage multi-panels may include pre-existing phage isolates as well as the de novo isolation of novel phages from samples taken at the water site. Thus, in one embodiment, the step of producing the infective (virulent) phage panel may further include screening and isolating naturally occurring phage active against the selected bacterial population. In another embodiment, it may be unnecessary to screen for phages where the suspect bacterial populations are already known or suspected. Phages may be isolated by a number of methods, including enrichment methods or any technique involving the concentration of phage from environmental or industrial samples followed by screening the concentrate for activity against specific host targets.

Additionally, new methods for isolating phages are likely to be developed, and any phages isolated by these methods are also deemed covered by the claims of this invention. Given the high genetic diversity of phages, these naturally occurring phages will include those with novel genomic sequence as well as those with some percent of similarity to phages known to infect other bacterial clades. Most of the new phages are expected to be members of the taxonomic group Caudovirales, also generally referred to as the tailed phage. The use of phage in an infective cocktail is dependent on the phage's bacteriolytic activity. Bacteria targeted by treatment with phage or phage panels include any isolates present in the target water system.

Phages can be optimized for effectiveness by selection for naturally occurring variants, by mutagenesis and selection for desired traits, or by genetic engineering. Traits that might be optimized or altered include, but are not limited to, traits involved in host range determination, growth characteristics, improving phage production, or improving traits important for the phage delivery processes. Thus, in another aspect, the step of producing the infective phage panel includes creating engineered phages against the selected bacterial population. This will include phages created to have a broad host range. This may be the product of directed genetic engineering, for example.

Collectively, the phages pooled together are referred to herein as the infective phage multi-panel. Initial treatment of a target water system with the infective phage panel is ideally followed up by monitoring the effects of treatment on the selected bacterial subpopulation. Over longer periods of time, it may be necessary to alter the phage panel to confront bacteria that have developed resistance mechanisms to the infective phage panel. This is especially true if the phages isolated above ground and in the absence of salt are found to not be viable at down-hole formation conditions. Additionally, new bacterial species may begin to thrive in the absence of the initial selected bacterial subpopulation. Thus, the need may arise to alter the infective phage panel over time. New infective phage multi-panels may be created in response to either resistant strains or new bacterial populations causing biofilm fouling or bio-corrosion. The effectiveness of the infective phage panel is, in one embodiment, monitored by evaluating changes in phage and bacterial host populations within the system. One can either determine the presence of such bacterial populations directly, or simply monitor the formation of new biofilms and the reoccurrence of bio-corrosion events.

Large Scale Phage Production

Phages are produced, in one embodiment, using a standard liquid lysate method. It should be noted that industrial scale phage production has been achieved inadvertently by the dairy industry and historically by the acetone/butanol fermentation industry, which demonstrates the feasibility of aerobic and anaerobic phage production on this scale.

1. Prepare an exponentially (=OD600~0.3) growing stock of the target host bacteria in the volume of liquid corresponding to the desired final lysate volume. This is done by inoculating the media from a stationary stage liquid culture to a very low cell density (OD600~0.01) and monitoring growth spectrophotometrically until the desired OD is reached.

2. Inoculate this culture with phage to a moi (multiplicity of infection=ratio of phage particles to individual host cells) of 0.1 to 0.001.

3. The culture is then incubated until lysis is observed; incubation is typically overnight but can take several days depending on the host growth rate. At this point, the lysate is ready for purification of the phage particles away from both bacterial cell debris and the components of the culture media. This is accomplished first by vacuum filtration through a filter series with the final pore size being 0.2 µm. Finally, tangential flow filtration will be used to replace components of the media with 10 mM phosphate buffer and, if necessary, to concentrate the phage.

Since phages are notoriously hardy, they may be concentrated, freeze dried and stored for long periods of time without loss of effectiveness. Phages may also be encapsulated with a coating that dissolves in water. This allows phage panels (cocktails) and multi-panels to be shipped to remote locations for use. It allows the manufacture to be made at optimized central locations. While it is desirable that steps 1-6 be performed "on location," it is sometimes preferred that the manufacture of the large scale phage panel be centralized in locations where the necessary equipment and resources are readily available.

In this specification, the invention has been described with reference to specific embodiments. It will, however, be evident that various modifications and changes can be made thereto without departing from the broader spirit and scope of the invention as set forth in the appended claims. The specification is, accordingly, to be regarded in an illustrative rather than a restrictive sense. Therefore, the scope of the invention should be limited only by the appended claims.

The invention claimed is:

1. A continuous process for replication of bacteriophage comprising:
   continuously passing a solution of target bacteria and a solution of bacteriophage virulent for target bacteria into an inlet of a vessel that also has an outlet for removing a solution containing replicated bacteriophage in a manner that the solutions mix and flow together from the inlet to the outlet while bacteriophage is replicating and continuously removing a mixed solution with an enhanced concentration of bacteriophages;
   wherein the flow rate of the inlet solution containing target bacteria and the flow rate of the outlet solution containing bacteriophage virulent for target bacteria are adjusted to obtain sufficient time of the solutions in the vessel to effect substantial destruction of target bacteria.

2. The process of claim 1 wherein the solution of target bacteria is taken from a "frac" water pond or "frac" water storage tank.

3. The process of claim 2 wherein the target bacteria are sulfate reducing bacteria and/or acid producing bacteria.

4. The process of claim 2 wherein the solution of target bacteria is taken from a "frac" water pond or "frac" water storage tank and the target bacteria concentration increased by filtering out some of the water.

5. The process of claim 1 wherein analysis of the cell concentration of at least one of the outlet solution, the inlet bacteria solution, and the inlet bacteriophages solution is utilized by a control means to adjust the flow rates of one or more of the inlet solutions.

6. The process of claim 1 wherein a second target bacteria inlet solution is used to supplement the bacteria in the first bacteria solution inlet.

7. The process of claim 1 wherein the target bacteria are sulfate reducing bacteria and/or acid producing bacteria.

8. The process of claim 1 wherein the virulent bacteriophages are obtained from a bacterial source indigenous to the location where it is to be applied to remediate biofouling.

9. The process of claim 1 wherein the virulent bacteriophages are concentrated by mixing bacteriophages with target bacteria for which they are specifically virulent for sufficient residence time of at least 20 minutes in a flowing stream in a vessel to allow the bacteriophages to lyse the bacteria, thus, proliferating the bacteriophage.

10. The process of claim 1 wherein the process is continuous wherein target bacteria solution comprises "produced" or flow-back water from a hydrofracking operation in a oil or gas well reservoir.

11. The process of claim 10 wherein the target bacteria are isolated from water indigenous to the location where bacteriophage replicated from it is to be applied to remediate biofouling and wherein said bacteria is cultured to produce a more concentrated solution than in the indigenous water.

12. The process of claim 1 wherein the solution of bacteriophages is supplied by recycle of a portion of the withdrawn, concentrated bacteriophage.

13. The process of claim 1 wherein indigenous target bacteria are supplemented with target bacteria from a non-indigenous source.

* * * * *